United States Patent [19]

Petrofsky

[11] Patent Number: 5,048,522

[45] Date of Patent: * Sep. 17, 1991

[54] POWER MUSCLE STIMULATOR

[75] Inventor: Steven H. Petrofsky, Dayton, Ohio

[73] Assignee: Therapeutic Technologies, Inc., Tampa, Fla.

[ * ] Notice: The portion of the term of this patent subsequent to Mar. 5, 2008 has been disclaimed.

[21] Appl. No.: 637,606

[22] Filed: Jan. 2, 1991

Related U.S. Application Data

[63] Continuation of Ser. No. 509,565, Apr. 13, 1990, Pat. No. 4,996,987, which is a continuation-in-part of Ser. No. 349,856, May 10, 1989.

[51] Int. Cl.$^5$ .............................................. A61N 1/00
[52] U.S. Cl. ................................ 128/421; 128/423 R; 128/783
[58] Field of Search ........... 128/421, 734, 422, 423 R, 128/783

[56] References Cited

U.S. PATENT DOCUMENTS

| | | | |
|---|---|---|---|
| Re. 32,091 | 3/1986 | Stanton | 128/423 W |
| 1,908,688 | 5/1933 | Call | 128/421 |
| 2,375,575 | 5/1945 | Morland et al. | 128/421 |
| 3,261,358 | 7/1966 | Bernard | 128/423 R |
| 3,796,221 | 3/1974 | Hagfors | 128/421 |
| 3,911,930 | 10/1975 | Hagfors | 128/421 |
| 4,177,819 | 12/1979 | Kofsky et al. | 128/422 |
| 4,324,253 | 4/1982 | Greene | 128/421 |
| 4,349,030 | 9/1982 | Belgard et al. | 128/419 PG |
| 4,372,319 | 2/1983 | Ichinomiya et al. | 128/421 |
| 4,398,537 | 8/1983 | Holmbo | 128/429 R |
| 4,431,002 | 2/1984 | Maurer et al. | 128/422 |
| 4,442,839 | 4/1984 | Maurer et al. | 128/419 R |
| 4,535,777 | 8/1985 | Castel | 128/421 |
| 4,556,064 | 12/1985 | Pomeranz et al. | 128/423 R |
| 4,571,556 | 2/1986 | Gnerlich | 128/423 R |
| 4,640,286 | 2/1987 | Thomson | 128/421 |
| 4,693,254 | 9/1987 | Mickiewicz et al. | 128/421 |
| 4,759,368 | 7/1988 | Spanton et al. | 128/421 |
| 4,763,656 | 8/1988 | Nauman | 128/421 |
| 4,769,881 | 9/1988 | Pedigo et al. | 128/421 |
| 4,803,986 | 2/1989 | Dufresne et al. | 128/419 R |
| 4,803,988 | 2/1989 | Thomson | 128/421 |
| 4,813,418 | 3/1989 | Harris | 128/421 |
| 4,870,341 | 9/1989 | Pihl et al. | 128/734 |
| 4,901,725 | 2/1990 | Nappholz et al. | 128/734 |
| 4,917,093 | 4/1990 | DuSresne et al. | 128/734 |
| 4,919,138 | 4/1990 | Nordeuströom | 128/421 |
| 4,919,139 | 4/1990 | Brodard | 128/422 |
| 4,977,895 | 12/1990 | Tannenbaum | 128/421 |
| 4,996,987 | 3/1991 | Petrofsky | 128/421 |

FOREIGN PATENT DOCUMENTS

| | | | |
|---|---|---|---|
| 0057944 | 8/1982 | European Pat. Off. | 128/421 |
| 1485372 | 9/1977 | United Kingdom | 128/421 |

OTHER PUBLICATIONS

International Search Report PCT/US90/03170 Mailed Mar. 7, 1991.

Primary Examiner—Francis Jaworski
Assistant Examiner—George Manuel
Attorney, Agent, or Firm—Wood, Herron & Evans

[57] ABSTRACT

A method and apparatus are provided for electrically stimulating muscle of individuals having little or no nerve damage so the muscle can be power contracted with little pain to the individual. A therapeutic current is applied to the muscle which includes alternating desensitizing and stimulus currents. The desensitizing current is a high frequency, low amplitude current to desensitize the muscle and the stimulus current is a low frequency, high amplitude current to stimulate the muscle. The currents alternate at a point where the amplitude and slope of the two currents are substantially identical to avoid abruptions in the current. An onset failure monitor circuit is also provided to detect an increase in skin/electrode impedance indicative of possible subsequent failure of the skin-electrode connection or electrode failure.

19 Claims, 4 Drawing Sheets

POWER MUSCLE STIMULATOR

RELATED APPLICATION

This is a continuation of application Ser. No. 509,565, filed Apr. 13, 1990, now U.S. Pat. No. 4,996,987, which is a continuation-in-part of my U.S. patent application Ser. No. 07/349,856, filed May 10, 1989 of the same title. The disclosure of that application is incorporated herein by reference.

BACKGROUND OF THE INVENTION

The present invention relates to functional electrical stimulation (FES) of muscles to induce contraction thereof with electrical stimulus. More specifically, the present invention relates to electrically stimulating and exercising muscles to build muscle mass especially in patients having only partial or no nerve damage who might otherwise experience intolerable pain levels with such muscle stimulation.

Much work has been done in the area of functional electrical stimulation of muscles. Most notably, substantial success has been achieved in the area of building muscle mass of severely nerve damaged individuals such as paraplegics and/or quadriplegics by electrically stimulating the muscles sufficiently to induce work-producing contraction of the muscles ("power contraction").

The use of functional electrical stimulation for paralyzed individuals has been known to provide substantial health benefits in addition to building muscle mass. By way of example, U.S. Pat. No. 4,499,900, the disclosure of which is incorporated herein by reference, discloses an exercise bicycle which utilizes functional electrical stimulation to induce sufficient contraction of a paralyzed individual's leg muscles such that the individual's legs pedal an exercise bicycle through a complete and rigorous exercise routine thereby exercising otherwise atrophy-prone muscles. The exercise bicycle of that patent not only helps paraplegics and quadriplegics develop muscle mass, but improves their cardiovascular system, reduces and even eliminates pressure sores, and generally renders such individuals more physically fit with an improved prognosis for longevity. It would be desirable to provide such advantages to individuals having less nerve impairment than quadriplegics and paraplegics already aided by such a device.

In systems of the prior art adapted to provide power contraction of human muscle, the electrical therapeutic current stimulus coupled to the muscle typically has characteristics which, if applied to an individual without severe nerve damage associated with the muscles to be stimulated, could cause excruciating pain. Thus, individuals who are either not nerve-damaged or have only partial (but relevant) nerve-damage may not be able to take full advantage of functional electrical stimulation without risking severe pain. Thus, use of prior art "power contracting" type of systems have generally been limited to paraplegics and/or quadriplegics. However, many individuals, not just those suffering from severe nerve damage, could benefit from electrically-induced power contraction exercise therapy.

SUMMARY OF THE INVENTION

The present invention provides an electrical power muscle stimulator which may be utilized by individuals having little or no nerve damage but without the pain and other drawbacks which might otherwise accompany the use of functional electrical stimulation in such individuals. To this end and in accordance with one aspect of the present invention, a high frequency, low amplitude current ("desensitizing current") is first applied to the muscle to desensitize the muscle, and immediately thereafter a low frequency, high amplitude current ("FES current") which is continuous with the desensitizing current, is synchronously applied to power contract the muscle. More specifically, the FES current has a slope and an amplitude substantially identical to the slope and amplitude of the desensitizing current as the FES current begins substantially simultaneously with the desensitizing current termination so that no abrupt discontinuity occurs between the currents. Preferably, the desensitizing current is then immediately reapplied in a similar continuous manner upon termination of the FES current.

The desensitizing and FES currents may be separately generated and then selectively combined to produce a continuous, therapeutic current with alternating periods of desensitizing and FES currents. Preferably, the separately generated FES and desensitizing currents are simultaneously and continuously digitally synthesized from a common time base to permit synchronous switching therebetween such that the continuous, therapeutic current is produced without abruptions which might reduce or overcome the advantageous numbing effect achieved. The continuous, therapeutic current thus produced is believed to generally numb the area of the muscle to reduce response to painful stimulus while also providing stimulus to power contract the muscle such that non-nerve damaged individuals may obtain the advantages of functional electrical stimulation without the drawbacks which might otherwise be associated therewith.

The continuous, therapeutic current produced in accordance with the present invention includes a muscle contracting or "stim" segment and a desensitizing or "rest" segment during which the muscle is not power contracted, the stim segment being the basis of actual stimulation of muscles. The FES current to be applied to the muscle during the stim segment is, therefore, preferably selected to maximize training or the effective building of muscle mass. The stim segment FES current is further preferably selected to reduce even further the risk of pain associated with use of the power muscle stimulator of the present invention.

It is known that pain is reduced by the use of a continuously varying biphasic (having generally positive and negative amplitude portions relative an average or reference separated by one zero-crossing of the reference during any one fundamental period) electrical stimuli such as is produced by a current having a sinewave characteristic. Thus, one possible therapeutic current which may be employed in the present invention has a stim segment FES current which, over a fundamental period, is a simple sinewave.

In accordance with a yet further aspect of the present invention, a preferred stim segment FES current is utilized by which pain may be even further reduced in comparison to the sinewave stim segment FES current. The preferred stim segment FES current has a fundamental period during which a continuous, camelback, biphasic signal is generated. More specifically, the preferred stim segment FES current is continuous and biphasic, but has three portions separated by two zero crossings, relative an average or reference, rather than two portions separated by one zero crossing as would occur with a sinewave stim segment FES current. Further, the first and third portions of the continuous, camel-back, biphasic stim segment FES current are substantially identical in duration and magnitude relative the reference, while the second, intermediate portion is selected to have a duration equal to the sum of the duration of the first and third periods but a magnitude equal and of opposite polarity to the magnitude of either the first or third portions. As a consequence, the total energy output of both the first and third portions is equal, but of opposite polarity to the total energy output of the second portion.

The preferred stim segment FES current of the present invention is believed to be sufficient to power contract human muscle with little discomfort and with substantially reduced pain as compared to the sinewave stim segment, for example, such that muscles of non-nerve damaged individuals may be exercised with functional electrical stimulation with reduced risk of pain or worse. Further, when alternately applied to muscle in synchronization with the desensitizing current of the present invention, there is believed to be provided a power muscle stimulator which has a lesser pain level and which may therefore be used by even non-nerve damaged individuals to achieve the advantages and benefits of functional electrical stimulation without the pain or other drawbacks which otherwise might be associated therewith.

In accordance with a yet further aspect of the present invention, risk of accidental pain or injury encountered from improper connection between the stimulator and the muscle may be avoided by an "onset failure" monitoring system. As is well understood, therapeutic currents to be applied to the muscle are typically conducted over wires coupled to electrodes which are adhered to the skin over the muscle to be stimulated. It is not uncommon for an electrode to come loose from the skin or lose adhesion thereto. When the electrode comes loose, application of the therapeutic current could result in arcing which may cause pain or injury to the user. Prior art attempts to avoid such a risk are not believed to respond properly to such failures. I have determined that well before there is such a failure, the impedance between the electrode and the skin will increase above normal but well below the impedance level at which a loose electrode may lead to arcing. Thus, the present invention further provides a power muscle stimulator which indicates the onset of failure when the impedance at the skin-electrode interface becomes slightly elevated relative the normal skin-electrode interface impedance but still several orders of magnitude below failure condition so as to reduce the risk of pain or injury associated with failure of the electrode contact in the prior art.

These and other objects of the present invention shall become more apparent from a detailed description of the invention.

BRIEF DESCRIPTION OF THE DRAWINGS

The accompanying drawings, which are incorporated in and constitute a part of this specification, illustrate the invention and, together with the general description of the invention given above and the detailed description given below, serve to explain the principles of the invention.

DETAILED DESCRIPTION OF THE INVENTION

Figure 1:
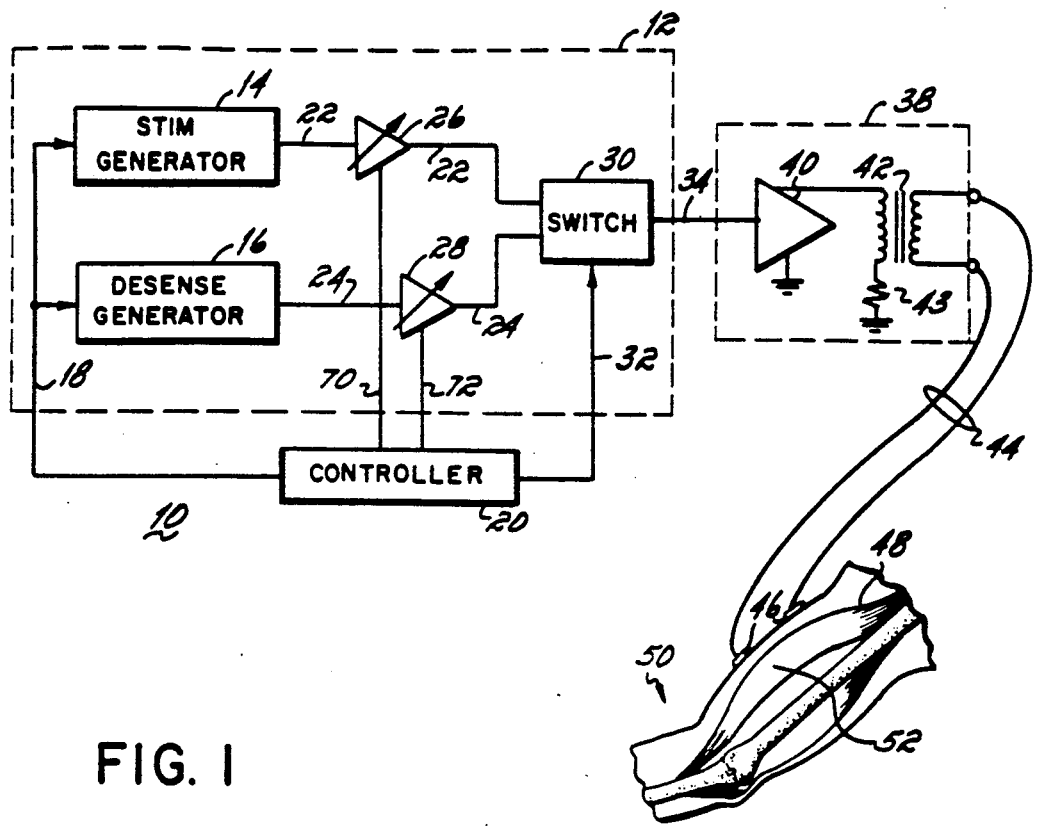
FIG. 1 is a block schematic diagram of a single channel power muscle stimulator in accordance with the principles of the present invention.
Figure 2:
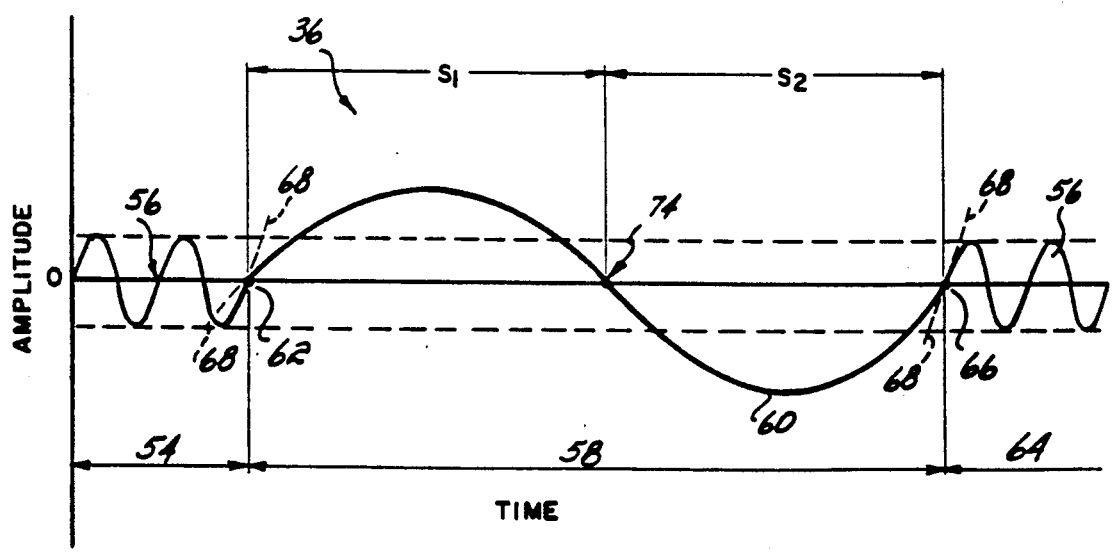
FIG. 2 is a diagram of a representative therapeutic current produced by the power muscle stimulator of FIG. 1.

With reference to FIG. 1 there is shown a single channel power muscle stimulator 10 adapted to produce a therapeutic current by which to provide functional electrical stimulation of muscle with reduced pain in accordance with the principles of the present invention. Power muscle stimulator 10 includes a driving signal generator 12 including a stim generator 14 and a desense generator 16 responsive to timing control signal 18 from controller 20. The outputs 22, 24 of generators 14, 16 are coupled through variable gain stages 26, 28 and then selectively combined at switch 30 in response to timing control signal 32 from controller 20 to produce on output 34 a voltage driving signal corresponding to the therapeutic current such as represented by exemplary waveform 36 of FIG. 2. Voltage driving signal on output 34 is coupled to output stage 38 including constant current amplifier 40 which in conjunction with transformer isolator 42 and 1 ohm sense resistor 43 produces the therapeutic current having a characteristic waveform as seen in FIG. 2. The therapeutic current thus produced is coupled over a pair of wires 44 to a pair of surface electrodes 46 adhered to the skin 48 of a human limb 50 in overlying relationship with muscle 52 to be electrically stimulated. Although referred to herein as a therapeutic current, one of ordinary skill in the art will readily appreciate that a therapeutic voltage or power could be employed.

As may be seen in FIG. 2, therapeutic current 36 preferably includes a first "rest" segment 54 during which there is provided a low amplitude, high frequency desensitizing current 56, followed immediately by a stim segment 58 during which there is provided one period of a high amplitude, low frequency FES current 60 wherein FES current 60 has a slope and amplitude substantially identical to the slope and amplitude of desensitizing current 56 as the FES current begins substantially simultaneously with the desensitizing current termination as at 62 to produce a substantially continuous therapeutic current with no abruption or discontinuities. Preferably, stim segment 58 is immediately followed by a further rest segment 64 during which the desensitizing current 56 is again provided having a slope and amplitude substantially identical to the slope and amplitude of FES current 60 as the desensitizing current begins anew substantially simultaneously with the FES current termination as at 66 to again avoid an abruption or discontinuity in the therapeutic current. The above sequence preferably is repeated to produce a substantially continuous therapeutic current having alternating segments of desensitizing and FES currents with the FES currents repeated at not more than about an 83.3 Hz repetition rate. Transitions 62 and 66 are shown at the zero crossing of the two currents as exemplified by the intersection of dotted line extensions 68 in FIG. 2 although other transition points may be selected as long as substantial identicality of the slope and amplitudes are achieved at the transition so as to produce a substantially continuous therapeutic current.

Preferably, stim generator 14 continuously provides a voltage signal corresponding to FES current 60 while desense generator 16 continuously provides a voltage signal corresponding to desensitizing current 56 and having an integral ratio of periods one to the other such that they will occasionally share zero crossings whereat the amplitude and slopes of the currents produced thereby are substantially equal. Controller 20 initiates each generator to maintain a common time base reference so that such zero crossings substantially coincide. Additionally, timing control signal 32 from controller 20 causes switch 30 to selectively pass one or the other of the signals from generators 14 and 16 so as to produce the aforesaid continuous therapeutic current. Further, controller 20 produces amplitude control signals 70, 72 by which to control the gain of stages 26, 28 so as to provide an exercise profile for repeated generation of the therapeutic current as will be described hereinafter.

Figure 3:
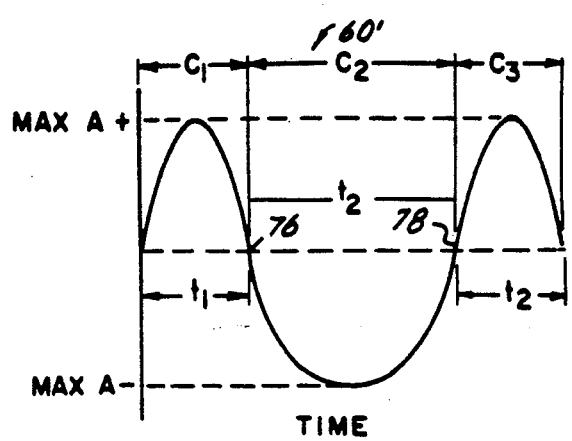
FIG. 3 is a diagram of a preferred FES current produced by the power muscle stimulator of FIG. 1 in accordance with the principles of the present invention.

FES current 60 is preferably selected to produce at least one period of a periodic stimulus signal such as a current having a sinewave characteristic as seen in FIG. 2 or having a camel-back characteristic as seen in FIG. 3. It is desired that FES current 60 have a sufficiently high amplitude and low frequency to induce power contraction of muscle 52. To this end, the maximum amplitude of FES current 60 is preferably between about 50 and 100 mA but may go as high as 150 mA. Also, the frequency of FES current 60 is preferably below about 7 KHz, and further preferably in the range of 1 KHz and 5 KHz.

Desensitizing current 56, on the other hand, preferably has a sufficiently high frequency and low amplitude to desensitize or numb the area of muscle 52 to reduce or cancel nerve response to pain-causing stimuli during the rest period without power contraction of muscle 52 and at a level sufficiently low as to not fatigue muscle 52 during rest segments 54 and 64. To this end, the maximum magnitude of desensitizing current 56 is preferably about one-half of the maximum magnitude of FES current 60 and at least one-fifth thereof but not more than about 50 mA. Also preferably, the frequency of desensitizing current 56 is at least about 7 KHz and preferably in the range of 10 KHz to 12 KHz. Thus, the frequency of FES current 60 is low relative the frequency of desensitizing current 56 while the amplitude of the two currents bear the opposite relative relationship.

Exemplary FES current 60 of FIG. 2 is a continuous, bi-phasic sinewave during one fundamental period thereof having two portions $S_1$ and $S_2$ of opposite polarity relative the reference of zero and separated by one zero crossing 74. The amplitude of portions $S_1$ and $S_2$ are of equal magnitude, but opposite sign. Although portion $S_1$ is shown as positive relative the zero references and portion $S_2$ is negative, an inverse sinewave could be utilized for FES current 60 provided transitions 62, 66 occur one-half period earlier relative the higher frequency sinewave of desensitizing current 56 to preserve substantial identicality of slopes and magnitudes between the currents as previously described.

An alternative and preferred FES current 60' is shown diagrammatically in FIG. 3. As seen in FIG. 3, preferred FES current 60' has three portions $C_1$, $C_2$ and $C_3$, each of which continuously varies from a reference (here, zero) to a maximum amplitude (Max A+ and Max A−) and then back to zero separated by two zero crossings 76, 78. However, first and third portions, $C_1$ and $C_3$, have one polarity relative the zero reference, and intermediate, second portion $C_2$ an opposite polarity relative thereto. FES current 60' is bi-phasic but would appear, if viewed on an oscilloscope, to have two humps like a camel back during one repetition (i.e., during a fundamental period) thereof. Thus, preferred FES current 60' has a fundamental period during which it is continuous, bi-phasic, and camel-back. Although portions $C_1$ and $C_3$ are shown having positive polarity and portion $C_2$ negative, the inverse would be acceptable, i.e., portions $C_1$, $C_3$ of negative polarity and portion $C_2$ of positive polarity. Of course the transition from and to the desensitizing current must still preferably meet the above-described requirements for substantially identical slopes and amplitudes thereat.

Significantly, the absolute magnitude of each of the three portions, $C_1$, $C_2$ and $C_3$, relative the zero reference is the same. Further significantly, the duration $t_1$ of portion $C_1$ is equal to the duration $t_3$ of portion $C_3$, and the duration $t_2$ of intermediate portion $C_2$ is equal to the sum of $t_1$ and $t_3$ (or twice either $t_1$ or $t_3$)

Due to time and amplitude relationships, the energy delivered to a muscle due to portion $C_2$ is equal to twice the energy delivered to a muscle due to either of portions $C_1$ and $C_3$. That is, the magnitude of the integral of both the first and third portions $C_1$ and $C_3$, relative the zero reference is equal to the magnitude of the integral of the second portion $C_2$ relative that reference. Similarly, the fundamental frequency of each of the first and third portions $C_1$, $C_3$ is twice the fundamental frequency of second portion $C_2$ (by way of example, about 5.33 KHz and 2.66 KHz, respectively).

During a normal exercise routine, it is preferred to ramp the magnitude of the therapeutic current over time in accordance with an exercise profile such as will be explained with reference to FIGS. 4, 5 and 5A. To this end, controller 20 preferably generates amplitude control signals 70, 72 by which the FES and desensitizing currents may be increased or decreased as desired.

An exercise profile designed to develop slow twitch muscles which provide endurance preferably consists of (1) a period of zero amplitude (i.e., the muscles rest), followed by (2) an increasing amplitude ramp during which the amount of each muscle contraction is to increase to warm up the muscles and/or reduce pain, (3) a period of full amplitude for maximum exercise of the muscles, and (4) a decreasing amplitude ramp during which the amount of each muscle contraction is to decrease to relax the muscles. With reference to FIG. 4, such an exemplary slow twitch exercise profile is shown which preferably starts off with 15 seconds of zero or rest (80), then increases or ramps up uniformly for 3 seconds (82) to a maximum (84). The maximum level (84) is maintained for 12 seconds and then the level ramps down (86) over a period of 3 seconds to zero. The exercise profile may be repeated for a complete exercise regime, such as for 30 minutes, for example. A second profile designed to develop fast twitch muscle fibers which provide strength would not include a period of maximum level but rather consists of repetition of at least one zero-amplitude rest period followed by an increasing amplitude ramp (82) and immediately followed by a decreasing amplitude ramp (86).

Figure 4:
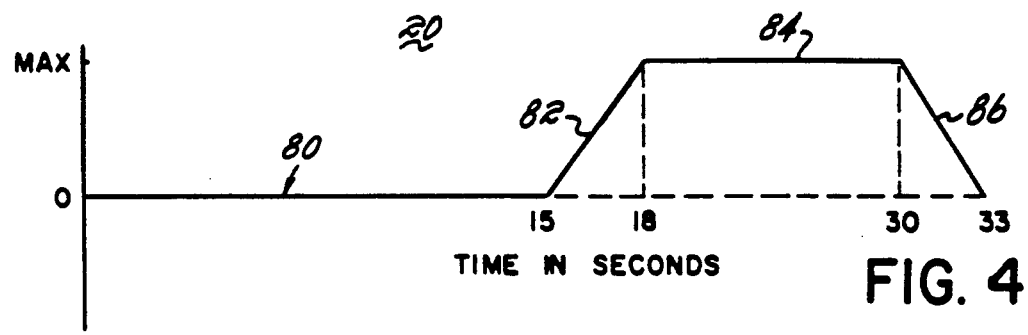
FIG. 4 is an exemplary exercise profile.
Figure 5:
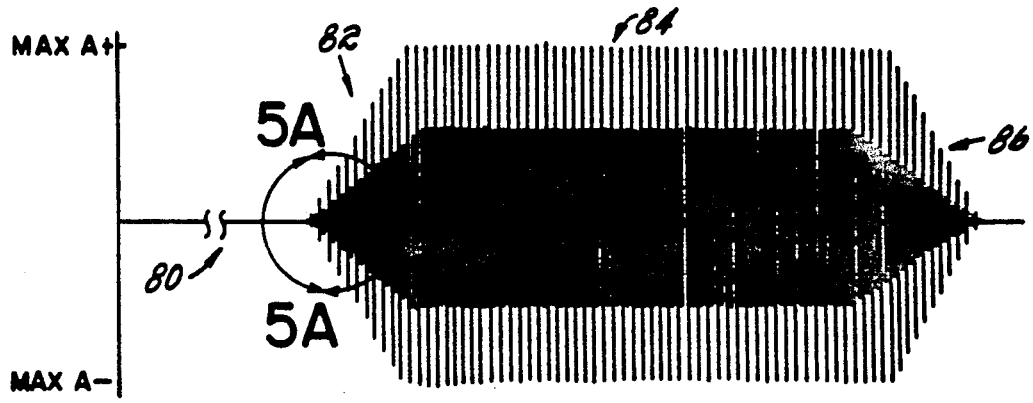
FIG. 5 is a diagram of an exemplary therapeutic current according to the exercise profile of FIG. 4.
Figure 5A:
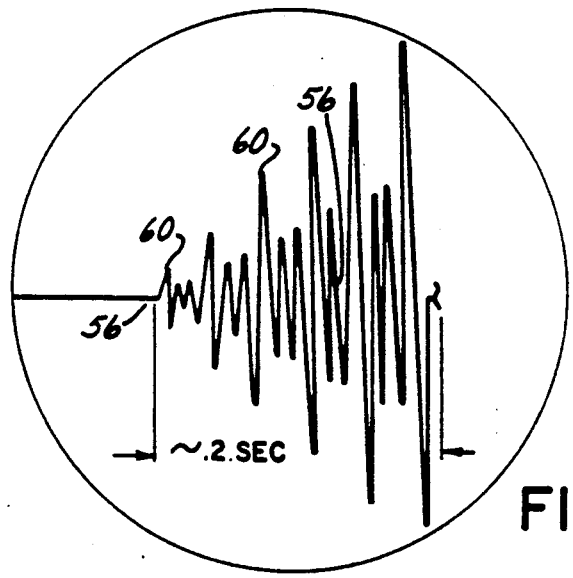
FIG. 5A is an expanded view of the portion of FIG. 5 encased by lines 5A—5A.

The amplitude control signals from controller 20 correspond, for example, to the profile of FIG. 4 and in cooperation with the gain stages 26, 28 cause therapeutic current 36 to increase or decrease in overall amplitude corresponding to the exercise profile and as shown diagrammatically in FIG. 5 wherein the therapeutic current begins, for example, with a relatively long rest period 86, a period 82 of increasing amplitude therapeutic current 36 (with synchronously alternating stim segments of FES current 60 and rest segments of desensitizing current 56 of increasing amplitude (see FIG. 5A)), a relatively long period 84 of maximum amplitude therapeutic current 36 (with alternating stim segments 58 having maximum amplitude FES current 60 and rest segments 54, 66 with maximum amplitude desensitizing current 56) and then concluding with a period 86 of stim segments 58 diminishing amplitude therapeutic current 36 (having alternating stim and rest segments of diminishing amplitude FES current 60 and desensitizing current 56). The first approximately two-tenths of one second of the ramp-up period 82 are shown in FIG. 5A for clarification.

In operation, the desensitizing and stim voltage driving signals are continuously generated by generators 14 and 16 under common control of controller 20. Switch 30 produces on its output a voltage driving signal corresponding alternately to one or the other of the stim and desensitizing voltage driving signals as selected by controller 20 to produce a continuous signal which switches between stim and desensitizing signals when their slopes and amplitudes are substantially equal. The profile of the signal may be varied for an exercise routine by gain stages 26, 28 also responsive to controller 20. The continuous voltage signal thus produced is converted to a continuous therapeutic current by output stage 38 and applied to the muscle 52. Consequently, muscle 52 is electrically stimulated with reduced pain by applying a high frequency, low amplitude current to the muscle to desensitize the muscle and immediately applying a low frequency, high amplitude current to the muscle to stimulate the muscle, the stimulating current having slope and amplitude substantially identical to the slope and amplitude of the desensitizing current as the stimulating current begins substantially simultaneously with the desensitizing current termination. Thereafter, the high frequency, low amplitude desensitizing current is reapplied to the muscle, the reapplied desensitizing current having slope and amplitude substantially identical to the slope and amplitude of the stimulating current as the reapplied desensitizing current begins substantially simultaneously with the stimulating current termination.

Figure 6:
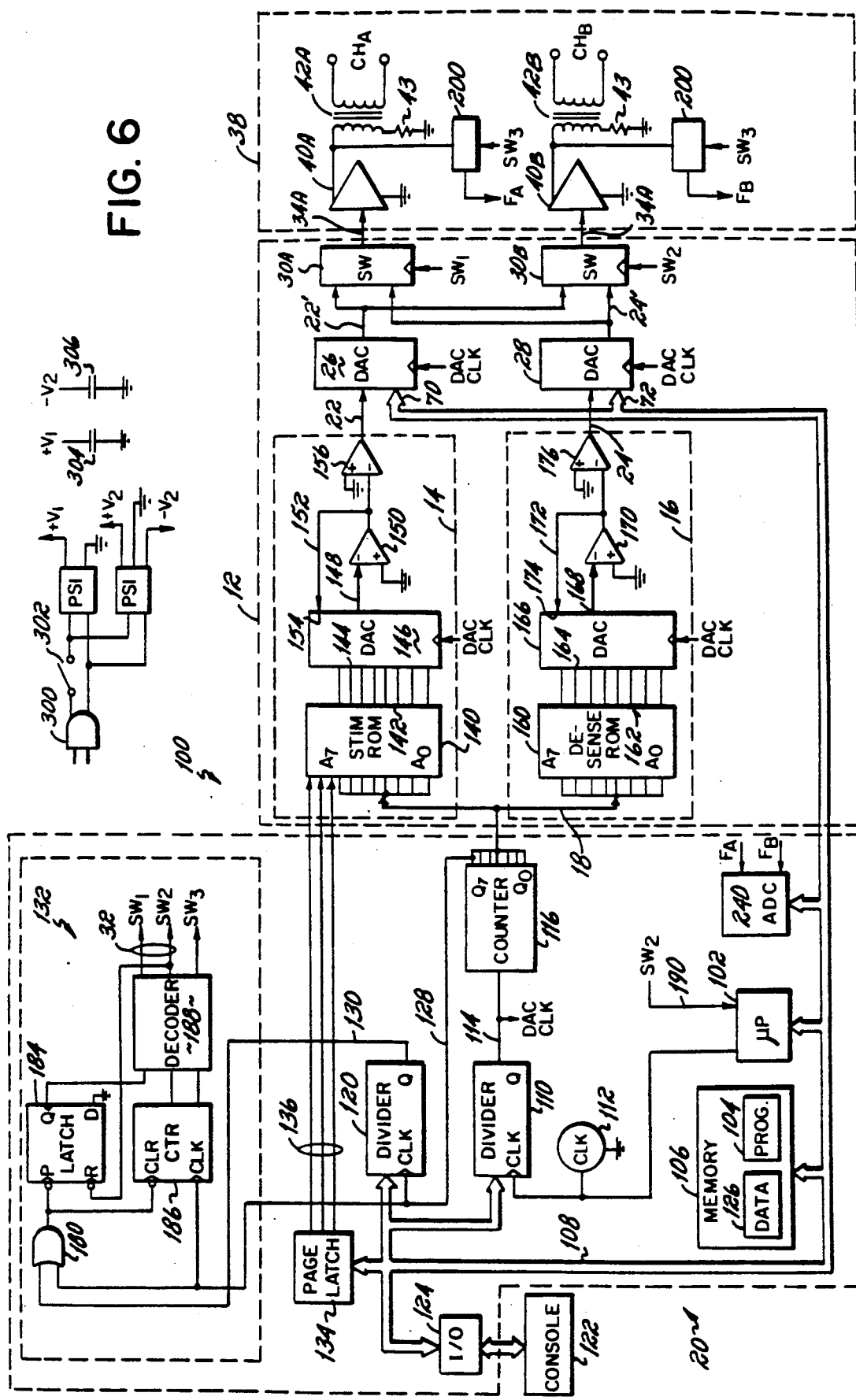
FIG. 6 is a schematic diagram of a two-channel power muscle stimulator similar to the single channel power muscle stimulator of FIG. 1.

Referring now to FIG. 6 there is schematically shown a two channel stimulator 100 similar to the power muscle stimulator of FIG. 1. Controller 20 of stimulator 100 is microprocessor-based and includes a microprocessor 102 operating under control of a program 104 stored in associated memory 106. Microprocessor 102 communicates with memory 106 and other portions of controller 2 via bidirectional address/data buss 108 as is well understood.

Microprocessor 102 loads first programmable divider 110 with a divisor of 8 for a 2 MHz clock 112 to produce as its output 114 a 250 KHz waveform clock signal. A binary counter 116 is responsive to the waveform clock signal to produce a binary count which repeats by cycles from a count of 6 to a count of 255 whereby to produce common timing control signals 18 for use by stim and desense generators 14, 16 as will subsequently be described.

Microprocessor 102 also loads second programmable divider 120 with a value corresponding to the repetition rate such as may be input by a technician via console 122 and input/output interface 124 and stored as data 126 in memory 106. Programmable divider 120 is responsive to the most significant bit (MSB) output 128 of programmable divider 110. Accordingly, to obtain a repetition rate of 60 Hz, for example, programmable divider 120 will be loaded with the value of 17 so as to produce on its output 130 a rep rate signal to selector circuit 132 which drives switches 30A and 30B to alternate at their outputs stim and desense voltage driving signals as appropriate.

Microprocessor 102 also loads into page latch 134 a code to determine the page selector outputs 136 thereof and which may be utilized by stim generator 14 to select the desired waveform characteristic of the FES current to be applied to the muscle during the stim segment With reference to generators 14, 16, each includes a memory 140, 160 such as a read-only-memory (ROM) or a programmable read only memory (PROM) with 8 bit data outputs. The lower order address lines $A_0$–$A_7$ of each memory 140, 160 are driven by common timing control signals 18 from counter 116 so as to repeatedly and synchronously sequence through lower order address locations 6–255 of memories 140, 160. The data outputs 142, 162 of memories 140, 160 are coupled to data inputs 144, 164 of respective clocked 8-bit digital-to-analog (D/A) converters 146, 166 such as Part No. AD7524 available from Analog Devices, Norwood, Mass. If such multiplying D/A converters are used, the $V_{REF}$ inputs are preferably coupled directly to $+V_1$ The analog outputs 148, 168 of converters 146, 166 are amplified by operational amplifiers 150, 170 in conjunction with feedback of the outputs 152, 172 from amplifiers 150, 170 to the $R_{feedback}$ pin 154, 174 of converters 146, 166. The outputs 152, 172 are coupled to level shifting operational amplifiers 156, 176 to generate on outputs 22, 24 the respective biphasic stim and desensitizing voltage driving signals. Amplifiers 150, 170 are preferably configured to provide a low pass filter function such as with RC feedback (not shown) to have a cutoff of approximately 14 KHz to reduce noise from generators 14, 16.

To provide the desired desensitizing signals, memory 160 is programmed in locations 6 to 255 with digital words which provide a sinewave voltage driving signal on output 24 having a frequency of at least about 7 KHz and preferably between about 10–12 KHz. Similarly, to provide the desired stim signal, memory 140 has several pages each of which is selected in response to signals 136 from page latch 134. Stored in memory locations 6–255 of each such page are digital words corresponding to the desired FES current and preferably having a frequency not more than about 7 KHz and more preferably between about 1–5 KHz. For example, on page 1 of memory 140, the digital words stored in locations 6–255 produce a stim voltage driving signal on the output 22 corresponding to the FES current 60 of FIG. 2. Similarly, on page 2 of memory 140, the digital words stored in locations 6-255 produce a stim voltage driving signal on the output 22 corresponding to the FES current 60' of FIG. 3. Other stim voltage driving signals may be stored on other pages of memory 140 such as may be used to produce different frequency sinewave or camelback stim signals.

Preferably, the digital words stored in memory 140 to produce the stimulus current are confined to at least memory locations 31 to 230 of each page thereof with the beginning several locations (6-30) and ending several locations (231-255) storing digital words corresponding to at least one period of desensitizing current such that switching between the two signals may be made when both generators 14, 16 are outputting voltage driving signals corresponding to the desensitizing current such that the transitions will be more readily synchronous and without abruption.

To provide the exercise profile described previously, data 126 from memory 106 is utilized by microprocessor 102 to periodically provide digital words to respective gain stages 26, 28 for appropriate amplification of voltage driving signals 22, 24. To this end, gain stages 26, 28 are each preferably a clocked 8-bit D/A converter such as aforementioned Analog Devices Part No. AD7524 wherein the $V_{REF}$ inputs are now driven by voltage driving signals 22, 24 respectively and the data inputs are digital words defining amplitude control signals 70, 72 from microprocessor 102 by which to produce the appropriate amplified voltage driving signals 22', 24' each of which is coupled to respective switches 30A and 30B to define a two channel stimulator.

Switch 30A is responsive to switch signal $SW_1$ from selector circuit 132 and switch 30B is responsive to switch signal $SW_2$ from selector circuit 132. Each of switch signals $SW_1$ and $SW_2$ initially is in a state such that outputs 34A, 34B of each channel will correspond to the desensitizing current which is produced out of transformers 42A, 42B for each channel.

At the appropriate times designated as the repetition rate, switch signals $SW_1$ and $SW_2$ will change to a second state for a period of time sufficient to cause switches 30A, 30B to output to amplifiers 40A, 40B a signal corresponding to the desired FES current after which the switch signal will revert to its initial or first state and the desensitizing current will thereafter be output. Selector circuit 132 is configured to provide the necessary state changes in switch signals $SW_1$ and $SW_2$ such that for either of channels A and B of stimulator 100, the therapeutic current will begin with a low amplitude, high frequency desensitizing signal which terminates when the switch signal switches to the second state thereby causing a high amplitude, low frequency FES current to immediately begin and with the amplitude and slope of the FES current as it begins being substantially identical to the amplitude and slope of the desensitizing current as it terminates. When the switch signal reverts to its first state, the desensitizing current is immediately begun again and the FES current terminated and with the amplitude and slope of the desensitizing current as it is begun again being substantially identical to the amplitude and slope of the FES current as it terminates.

To achieve the foregoing time relationship, the most significant bit (MSB) $Q_7$ output 128 of counter 116 is utilized by selector circuit 132 such that all switch signal state transitions occur substantially simultaneously with reinitiation of the count for addressing memories 140, 160 so as to cause such transitions at the appropriate zero crossings of the desensitizing and FES currents. More particularly, MSB output 128 of counter 116 is further divided by programmable divider 120 to produce a rep rate signal 130 which changes state after each repetition rate interval. The rep rate signal 130 and MSB output 128 are each inputs to OR gate 180, the output of which drives the inverting P input of latch flip-flop 184 and the inverting clear input of counter 186. The clock input of counter 186 is also driven by the MSB output 128. Counter 186 provides a two bit binary count to decoder 188 which produces the appropriate output states for switch signals $SW_1$ and $SW_2$ when enabled by the Q output of flip-flop 184. Switch signal output $SW_2$ from decoder 188 is also utilized to reset flip-flop 184 to provide the appropriate switch signals as will now be described.

When both inputs to OR gate 180 go low, flip-flop 184 is enabled and counter 186 is reset after which it will provide a binary count between 0-3 in response to pulses from MSB output 128. Decoder 188 is responsive to flip-flop 184 such that when it is not enabled, decoder 188 puts switch signals $SW_1$ and $SW_2$ in their initial state such that desensitizing current may be applied from both of channels A and B. Also, a third switch signal $SW_3$, for purposes to be described hereinafter, will be placed in its initial state. When flip-flop 184 enables decoder 188, switch signals $SW_1$, $SW_2$ and $SW_3$ are varied in response to counter 186 as will now be described.

When the count from counter 186 is "0", decoder 188 will cause switch signals $SW_1$ and $SW_2$ to assume the first state (whereby desensitizing current may be applied from both channels A and B). Also switch signal $SW_3$ will assume the second state for purposes to be described below. At the next pulse from MSB output 128, the count from counter 186 is "1" which will cause switch signal $SW_1$ to assume the second state (whereby FES current may be applied from channel A) and $SW_2$ to assume the first state (whereby desensitizing current may be applied from channel B). Switch signal $SW_3$ will assume its first state. At the next pulse from MSB output 128, the count from counter 186 is a "2" which causes decoder 188 to change switch signal $SW_1$ back to its first state and switch signal $SW_2$ to its second state (whereby desensitizing current may be applied from channel A and FES current may be applied from channel B). Switch signal $SW_3$ remains in its first state. When the count from counter 186 goes to "3", switch signals $SW_1$ and $SW_2$ both are caused to assume the first state such that desensitizing current may be applied from both channels A and B. The state transition of $SW_2$ from its second state to its first state resets latch 184 which disables decoder 188 whereafter switch signals $SW_1$, $SW_2$ and $SW_3$ remain in their first state (desensitizing current may still be applied from both of channels A and B). This transition of switch signal $SW_2$ prevents any further change in the switch signal states from decoder 188 until flip-flop 184 is again enabled.

The transition of switch signal $SW_2$ from its second to its first state also results in an interrupt 190 to microprocessor 102 if it has not masked input 190 as will be understood by those familiar with microprocessors. When microprocessor 102 acknowledges the interrupt, it evaluates data 126 previously stored therein regarding the desired exercise profile to determine if any of the driving signals should be amplitude adjusted for the exercise profile. If any adjustment is necessary, microprocessor 102 outputs new amplitude control signals 70, 72 to gain stages 26, 28. At this time, microprocessor 102 may also alter page latch 134 to select a new FES current.

In accordance with one aspect of the invention, there is also preferably provided in each channel an "onset failure" monitoring circuit 200 which monitors the therapeutic current as an input to isolation transformer 42 of that channel to determine the impedance of the wire, electrode and skin interconnection.

As FES current is applied to the muscle through the electrodes attached to the skin, there is the possibility of injury if the electrode comes loose from the skin or loses adhesion thereto. Prior attempts to avoid such problems have focused on determining when there is, in effect, an open circuit between the electrode and the skin such that application of electrical stimulus could result in arcing which may cause pain or injury to the user. It has been determined that the normal 800 or so ohm impedance at the skin-electrode interface will typically begin to increase well before an open circuit condition exists. To monitor for the onset of such an increase in impedance, "onset failure" peak detector monitor circuit 200 is provided to measure the skin-electrode interface impedance.

Figure 7:
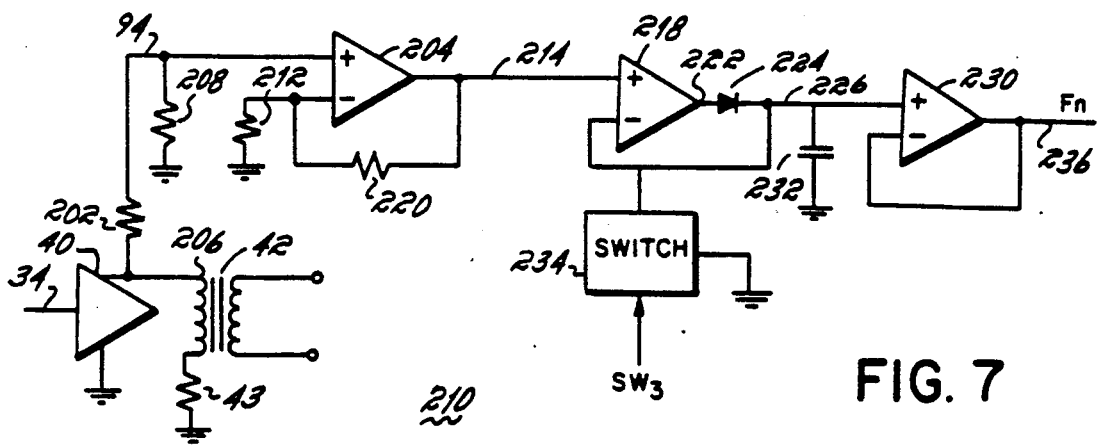
FIG. 7 is a detailed schematic of the onset failure monitoring circuit of the power muscle stimulator of FIG. 6.

As shown schematically in FIG. 7, the (+) input of amplifier 204 of onset failure monitoring circuit 200 is coupled via a 20K ohm resistor 202 to the input winding 206 of isolation transformer 42 and is also resistively coupled to ground via 10K ohm resistor 208. The (−) input of amplifier 204 is coupled to ground via 20K ohm resistor 212. The output 214 of amplifier 204 is coupled to the (+) input of amplifier 218 and via 10K ohm resistor 220 to its own (−) input. The output 222 of amplifier 218 is coupled through diode 224 to its (−) input and, via line 226, to the plus (+) input of amplifier 230 and capacitively coupled to ground via 0.01 microfarad capacitor 232. Line 226 is also selectively coupled to ground via switch 234 at the cathode end of diode 224 in response to a signal CL from microprocessor 102. Finally, output 236 of amplifier 230 is fed back to its (−) input and provides the impedance signal $F_n$ substantially corresponding to the impedance measured at the skin-electrode interface.

When switch signal $SW_2$ provides an interrupt to microprocessor 102, the impedance signals $F_A$ and $F_B$ are read and evaluated. To this end, the impedance signals are coupled via addressable analog-to-digital (A/D) converter 240 to microprocessor 102 whereat the values of signals $F_A$ and $F_B$ may be evaluated as described below. Switch 234 will be open during this time to allow circuit 200 to monitor the skin-electrode impedance. At the initiation of the next sequence, the second state of switch signal $SW_3$ closes switch 224 which shorts capacitor 232 to ground thereby clearing circuit 200 for a new impedance reading which will be made as the therapeutic current is applied after switch signal $SW_2$ again assumes its first state.

Microprocessor 102 compares the values of each of $F_A$ and $F_B$ against a reference impedance value at which the skin-electrode interface is still safely functional but at a level slightly above the normally expected and desirable skin-electrode impedance. The reference impedance value is also several orders of magnitude less than would be seen upon failure of the interface which may approach an open-circuit condition. After microprocessor 102 obtains impedance values $F_A$ and $F_B$, capacitor 232 will be grounded through switch 234 before the next progression of counter 186 preparatory to reapplying FES current from either channel. If $F_A$ or $F_B$ exceeds the reference impedance value by an amount still within an acceptable range but indicative of possible future failure, stimulator 100 will be disabled and an alarm (not shown) given. In a preferred embodiment, the reference impedance value is selected as 1K ohm. If $F_A$ or $F_B$ exceed that reference impedance value by at least 50%, although a lower level of 20% could be used, microprocessor 102 causes a shutdown of stimulator 100 such that no further therapeutic current may be output therefrom. Also, an alarm (not shown) may be produced. Additionally, if the measured impedance value is so low as to suggest a short circuit, such as below 50 ohms, stimulator 100 may also be shut down and an alarm issued.

In operation, microprocessor 102 executes the program 104 in memory 106 and acquires the therapy parameters from a technician through console 122 and I/O interface 124. From these parameters, microprocessor 102 determines which page of memory 140 to select, the repetition rate and the exercise profile (i.e., the current amplitudes for each time portion of the therapy session) and writes this into data portion 126 of memory 106. Thereafter, dividers 110 and 120 are programmed and controller 20 begins to produce common timing control signals (address signals) 18 for use by the memories 140, 160 of generators 14, 16. Also, amplitude control signals 70, 72 are periodically provided to gain stages 26, 28 to provide the desired exercise profile. Still further, switch signals $SW_1$ and $SW_2$ (timing control signals 32) are applied to switches 30A and 30B to obtain the desired continuous therapeutic current having desensitizing and FES currents which alternate without abruption. At each repetition, onset failure monitor circuits 200 will be examined and then reset and the therapy permitted to continue until completed or until a potential failure is indicated at which time stimulation 100 is disabled.

Stimulator 100 may be powered from a 120 VAC supply through plug 300. Plug 300 is selectively coupled to power supplies PS1 and PS2 via on/off switch 302. Power supplies PS1 and PS2 include appropriate transformers, diode bridges and voltage regulators as are conventional to provide $+V_1$ from PS1 and each of $+V_2$ and $-V_2$ from PS2. Power supply PS1 produces $+V_1=5$ volts, for example, to provide a source of power for the digital logic circuitry as is conventional. Power supply PS2 produces $+V_2=12$ volts and $-V_2=-12$ volts, for example, to provide a source of power for amplifiers 156, 176, 40A and 40B. As indicated at 304, 306, the $+V_2$ and $-V_2$ outputs of PS2 are preferably capacitively coupled to ground through 6,800 microfarad capacitors to allow nonsagging of the therapeutic current.

By virtue of the foregoing, there is thus provided an apparatus and method to accomplish electrical stimulation of muscle with little or no pain.

While the present invention has been illustrated by the description of alternative embodiments, and while the embodiments have been described in considerable detail, it is not the intention of the applicant to restrict or in any way limit the scope of the appended claims to such detail. Additional advantages and modifications will readily appear to those skilled in the art. For example, while stimulation 100 has been shown as a two channel stimulation, it could readily be expanded to three or more channels. Similarly, while switch signals SW₁ and SW₂ have been described as assuming their second states at different times, they could be switched together rather than sequentially, for example to simultaneously stimulate an agonist muscle and an antagonist muscle to provide unloaded isometrical exercise of a muscle.

The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A method for electrically stimulating a muscle with reduced pain comprising:
   applying a high frequency, low amplitude, continuously varying current to said muscle to densensitize said muscle; and
   immediately applying a low frequency, high amplitude, continuously varying current to said muscle to stimulate said muscle, said stimulating current have slope and an amplitude substantially identical to the slope and amplitude of said densensitizing current as said stimulating current begins substantially simultaneously with termination of said densensitizing current.

2. The method of claim 1 further comprising:
   immediately reapplying the high frequency, low amplitude, continuously varying densensitizing current to said muscle, said reapplied densensitizing current having slope and an amplitude substantially identical to the slope and amplitude of said stimulating current as said reapplied densensitizing current begins substantially simultaneously with termination of said stimulating current.

3. The method of claim 2 further comprising:
   continuously generating a high frequency, low amplitude first driving signal corresponding to said desensitizing current;
   continuously generating a low frequency, high amplitude second driving signal corresponding to said stimulating current;
   alternately converting said first and second driving signals to their respective desensitizing and stimulating currents to produce a continuous therapeutic current having alternating desensitizing and stimulating currents for application to the muscle.

4. The method of claim 1, the maximum magnitude of said stimulating current being at least twice the maximum magnitude of said desensitizing current.

5. The method of claim 4, the maximum magnitude of said stimulating current being not more than about five times the maximum magnitude of said desensitizing current.

6. The method of claim 1, said stimulating current frequency being less than about 7 KHz.

7. The method of claim 1, said stimulating current frequency being less than about 5 KHz.

8. The method of claim 7, said stimulating current frequency being greater than about 1 KHz.

9. The method of claim 1, said desensitizing current frequency being greater than about 7 KHz.

10. The method of claim 1, said desensitizing current frequency being at least about 10 KHz.

11. The method of claim 10, said desensitizing current frequency being less than about 12 KHz.

12. The method of claim 1 wherein said stimulus current begins and said desensitizing current terminates at respective zero amplitude crossings thereof.

13. An apparatus for stimulating muscle with reduced pain comprising:
   generator means for generating a therapeutic driving signal corresponding to a therapeutic current, said therapeutic driving signal having a high frequency, low amplitude portion and a low frequency, high amplitude portion;
   converting means for converting said therapeutic driving signal into said therapeutic current, said therapeutic current having a high frequency, low amplitude, continuously varying current corresponding to said high frequency, low amplitude driving signal portion and a low frequency, high amplitude, continuously varying current corresponding to said low frequency, high amplitude portion; and
   applying means for applying said therapeutic current to said muscle, said high frequency, low amplitude current densensitizing said muscle and said low frequency, high amplitude current stimulating said muscle, said low frequency, high amplitude current having slope and an amplitude substantially identical to the slope and amplitude of said high frequency, low amplitude current as said low frequency, high amplitude current begins substantially simultaneously with termination of said high frequency, low amplitude current.

14. The apparatus of claim 13 wherein said generating means includes:
   first generating means for continuously producing a high frequency, low amplitude first driving signal;
   second generating means for continuously producing a low frequency, high amplitude second driving signal; and
   switching means for switching between said high frequency, low amplitude driving signal and said low frequency, high amplitude driving signal when the slope and amplitude of said first and second driving signals are substantially identical.

15. The apparatus of claim 14 further comprising:
   onset failure circuit means for monitoring impedance to which said applying means is coupled.

16. The apparatus of claim 15, further comprising means responsive to said onset failure circuit means for shutting down the apparatus if the impedance being monitored exceeds a safe level of skin-electrode impedance.

17. The apparatus of claim 13 further comprising:
   gain stage means for adjusting the amplitude of said stimulating and desensitizing signals in accordance with an exercise profile.

18. The apparatus of claim 13 further comprising gain stage means for independently adjusting the amplitude of said stimulating signal and said desensitizing signal in accordance with an exercise profile.

19. A method for electrically stimulating muscle with reduced pain comprising:
   applying a low frequency, high amplitude, continuously varying current to said muscle to stimulate said muscle; and
   immediately applying a high frequency, low amplitude, continuously varying current to said muscle to densensitize said muscle, and desensitizing current having slope and an amplitude substantially identical to the slope and amplitude of said stimulating current as said desensitizing current beings substantially simultaneously with termination of said stimulating current.

* * * * *